United States Patent [19]

Mitsuya et al.

[11] Patent Number: 4,704,357
[45] Date of Patent: Nov. 3, 1987

[54] IMMORTALIZED T-LYMPHOCYTE CELL LINE FOR TESTING HTLV-III INACTIVATION

[75] Inventors: Hiroaki Mitsuya, Rockville; Samuel Broder, Bethesda, both of Md.

[73] Assignee: United States of America as represented by the Department of Health and Human Services, Washington, D.C.

[21] Appl. No.: 781,461

[22] Filed: Sep. 30, 1985

[51] Int. Cl.⁴ .......................... C12N 5/00; C12N 7/04; C12Q 1/18
[52] U.S. Cl. ............................ 435/32; 435/4; 435/5; 435/29; 435/235; 435/236; 435/240; 435/948; 514/42; 536/22
[58] Field of Search .................. 435/4, 5, 29, 32, 235, 435/236, 240, 241, 810, 948, 6; 536/22-24, 26; 514/42, 43, 45-46, 49, 50

[56] References Cited

U.S. PATENT DOCUMENTS

| | | | |
|---|---|---|---|
| 4,329,424 | 5/1982 | Machlowitz | 435/5 |
| 4,520,113 | 5/1985 | Gallo | 436/504 |
| 4,604,351 | 8/1986 | Amaral | 435/32 |
| 4,620,930 | 11/1986 | McDowell | 435/32 |
| 4,622,297 | 11/1986 | Kappner | 435/32 |

OTHER PUBLICATIONS

Popovic, M. et al., Science 224:497-500 (5-1984).
Mitsuya, H. et al., Science 225:1484-1486 (9-1984).
Mitsuya, H. et al., Science 226:172-174 (10-1984).
*Science*, vol. 229, pp. 563-570 (Aug. 9, 1985).
Proc. Natl. Acad. Sci., *Microbiology:* Folks et al., pp. 4539-4543, U.S.A. (1985).

*Primary Examiner*—Margaret Moskowitz
*Attorney, Agent, or Firm*—John S. Roberts, Jr.

[57] ABSTRACT

This invention is an immortalized T-cell clone, designated ATH8, which is highly sensitive to the cytopathic effect of HTLV-III. The ATH8 T-cell clone is used in mass screening systems to rapidly and easily determine the in vitro capacity of new drugs or other agents to inactivate or inhibit HTLV-III or related cytopathic retroviruses.

4 Claims, 4 Drawing Figures

Fig. 3
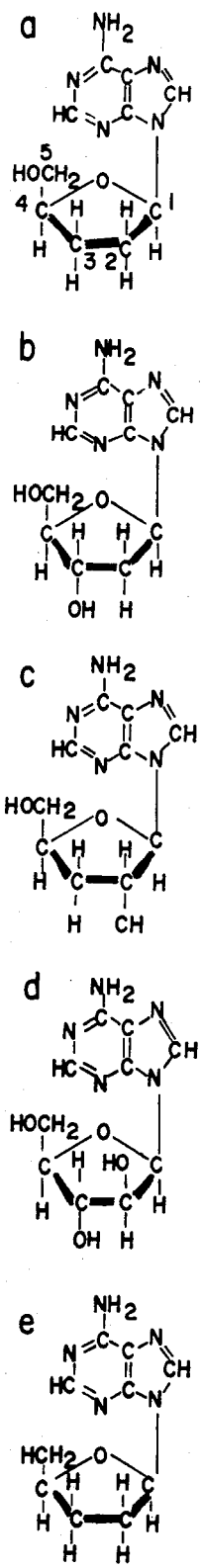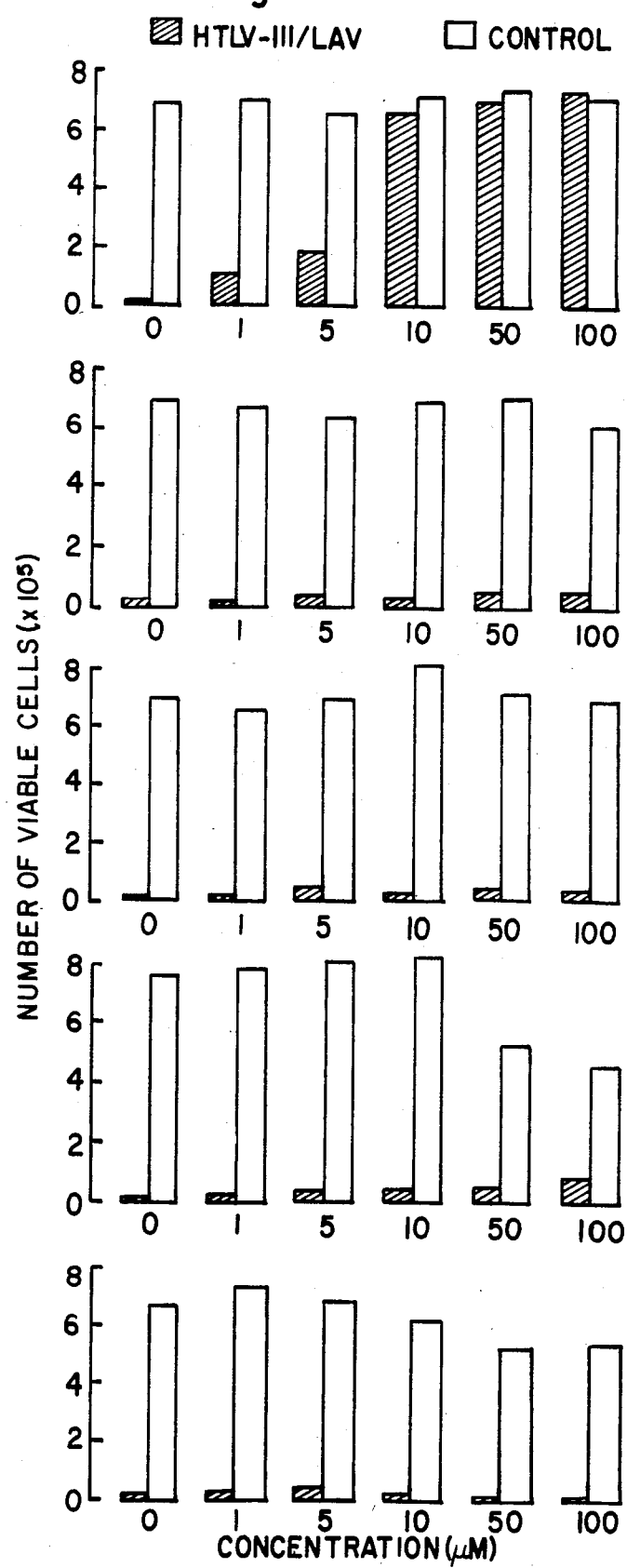

IMMORTALIZED T-LYMPHOCYTE CELL LINE FOR TESTING HTLV-III INACTIVATION

This invention is an immortalized T-cell clone, designated ATH8, which is highly sensitive to the cytopathic effect of HTLV-III. The ATH8 T-cell clone is used in mass screening systems to rapidly and easily determine the in vitro capacity of new drugs or other agents to inactivate or inhibit HTLV-III or related cytopathic retroviruses.

BACKGROUND OF THE INVENTION

Epidemiologic data strongly suggest that acquired immune deficiency syndrome (AIDS) is caused by an infectious agent transmitted by intimate contact or blood products. Though the disease is manifested by opportunistic infections, predominantly *Pneumocystis carinii* pneumonia and Kaposi's sarcoma, the underlying disorder affects the patient's cell-mediated immunity with absolute lymphopenia and reduced helper T-lymphocyte (OKT4+) subpopulation(s). Moreover, before a complete clinical manifestation of the disease occurs, its prodrome, pre-AIDS, is frequently characterized by unexplained chronical lymphadenopathy and/or leukopenia involving a helper T-cell subset. This leads to the severe immune deficiency of the patient, suggesting that a specific subset of T-cells is the primary taret for an infectious agent. Although patients with AIDS or pre-AIDS are often chronically infected with cytomegalovirus or hepatitis B virus, for various reasons these appear to be opportunistic or coincidental infections apparently not linked to the immunological response deficiency. The virus which causes AIDS, HTLV-III, is in the family of human T-cell lymphotropic retroviruses (HTLV) which comprises two major well characterized subgroups of human retroviruses, called human T-cell leukemia/lymphoma viruses, HTLV-I and HTLV-II.

Human T-lymphotropic virus type III (HTLV-III)/-lymphadenopathy-associated virus (LAV) is a newly discovered lymphotropic retrovirus which is cytopathic for helper/inducer T-cells in vitro. This virus is the etiologic agent of the acquired immunodeficiency syndrome (AIDS) and related diseases. Although a number of anti-viral agents are now being considered for the experimental therapy of AIDS, to date no therapy has been shown to cure HTLV-III/LAV infection or restore the underlying immunodeficiency. Moreover, the chronicity of infection and the propensity of the virus to infect the brain make it necessary to explore new classes of drugs which have the potential for oral administration and penetration across the blood-brain barrier.

The search for therapeutic reagents capable of inhibiting or inactivating HTLV-III/LAV has received a much publicized concerted effort on the part of scientists and doctors to find a cure for AIDS. The traditional in vitro screening systems involve the use of H9, CEM, MT-2, and/or MT-4 cells--clones of HTLV-III developed by Gallo and co-workers. These clones are described in Popovic, et al., *Science*, Vol. 224, p. 497 (1984) and Sarngadharan, et al., *Science*, Vol. 224, p. 506 (1984).

These older clones, however, are partially resistant to the cytopathic effects of HTLV-III. Because of this, use of H9, CEM, MT-2, or MT-4 cells requires an immunofluorescent assay or reversetranscriptase assay to monitor the effects of a putative drug or biologic that is being tested for an inhibitory effect against the virus.

On the other hand, the present invention—incorporating the newly developed cell line—is rapid, is useful for direct visual inspection (pellet size of target cell cultures) with confirmatory counts in a simple hemocytometer, and is highly sensitive. Furthermore, the present invention is readily adaptable for mass screening (hundreds of compounds at a time) and requires very little expenditure of labor and no unusual training on the part of the test operator. For additional comparisons of ATH8 to the other known clones, see Example 5.

STATEMENT OF DEPOSIT

Cell line ATH8 will be on deposit in the American Type Culture Collection in Rockville, Md., during the pendency of this application. The cell line will be available to the public as of the issue date of a patent on this subject matter, will be replaced if the culture mutates or becomes nonviable, and will be maintained for a term of 30 years, or five years after the last request for such deposit, or for the effective life of the patent, whichever is longest.

DESCRIPTION OF THE FIGURES

FIG. 3 shows the protection of ATH8 cells by adenosine congeners against the cytopathic effect of HTLV-III/LAV.

SPECIFIC DISCLOSURE

Figure 1:
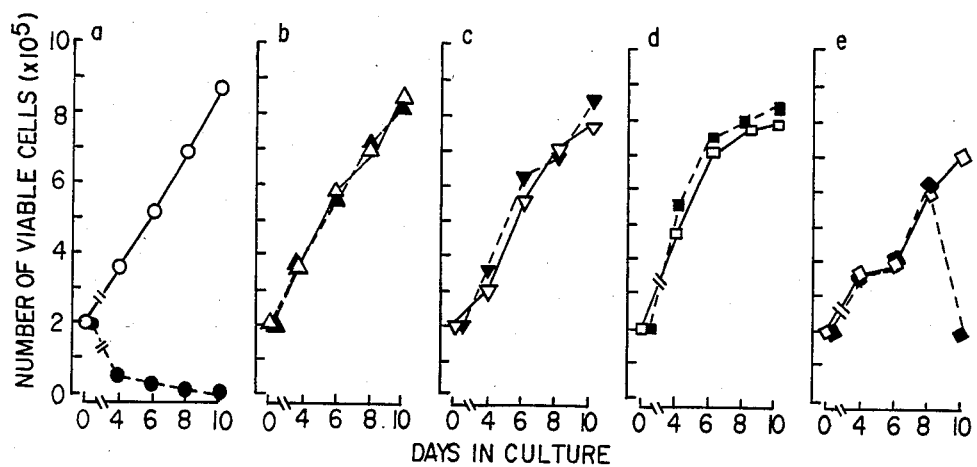
FIG. 1 shows the survival and growth of ATH8 cells in the presence of 2',3'-dideoxynucleosides, when exposed to HTLV-III/LAV.

A tetanus toxoid-specific T-cell line, established by repeated cycles of stimulation with antigen (Mitsuya, et al., *Science*, Vol. 225, pp 1484–1486, 1984) was cloned in the presence of lethally irradiated (12,000 rad) human T-lymphotropic virus type I (HTLV-I)producing MJ-tumor cells in 96-well microtiter culture plates. Clone ATH8 (obtained from a culture plated at 0.5 cells per well) was selected for drug screening on the basis of its rapid growth (in the presence of interleukin-2) and exquisite sensitivity to the cytopathic effect of HTLV-III/LAV. ATH8 clone bears several distinct copies of HTLV-I in its genome when assessed by Southern blot hybridization using a radiolabelled HTLV-I CDNA probe but does not produce detectable amounts of HTLV-I p24 gag protein. Example 1 and the accompanying chart show that ATH8 is significantly affected by the cytopathicity of HTLV-III. The above process produces an immortalized OKT4+T-cell specially cloned and selected on the basis of its sensitivity in vitro to pathogenic retrovirus (HTLV-III as well as LAV and ARV). It is lysed in the presence of HTLV-III within 4–5 days (all other known immortalized T-cell lines sensitive to HTLV-III are killed within 9–10 days).

The sensitivity of ATH8, as well as the other qualities noted in the background, is crucial for the rapid testing and evaluation of drugs used in therapy regimens against HTLV-III/LAV.

In general, various drugs or biologics are tested for their capacity to inactivate or inhibit HTLV-III by exposing ATH8 cells to HTLV-III followed by the addition of the sample drug. The results are then determined by direct visual inspection (pellet size of target cell cultures). These results may be confirmed using a simple hemocytometer. Example 2 illustrates the specifics of this process for several sample drugs. Note that results are obtained within 4-5 days.

In comparison, Example 4 shows the same test using H9 cells. As shown, the results are obtained after 8-10 days and require immunofluorescent assays or a reverse-transcriptase assay to monitor the effects of the sample drug being tested.

EXAMPLE 1

$10^5$ ATH8 cells were pre-exposed to 2 ug/ml polybrene for 30 minutes, pelleted, exposed to various amounts of HTLV-III$_B$, resuspended in 2 ml complete medium (RPMI supplemented with 15% undialysed, heatinactivated fetal calf serum, 4 mM L-glutamine, $5 \times 10^{-5}$ 2-mercaptoethanol, 50 U/ml penicillin, and 50 ug/ml streptomycin) containing 15% (vol/vol)-interleukin-2 (lectin-depleted; Cellular Products Inc., Buffalo, N.Y.), and incubated in culture tubes at 37° C. in 5% $CO_2$-containing humidified air. On day 7, the total viable cells were counted by the trypan blue dye exclusion method. Data are expressed as the arithmetic means ±1 standard deviation for duplicate determinations. See Table 1 below.

TABLE 1

| Cytopathic Effect of HTLV-III/LAV on ATH8 Cells | |
|---|---|
| Number of HTLV-III$_B$ Virus Particles Per Cell | Number of Viable ATH8 Cells ($\times 10^5$) |
| 0 | 3.37 ± 0.1 |
| 0.05 | 3.36 ± 0.04 |
| 0.5 | 3.26 ± 0.15 |
| 5 | 1.97 ± 0.2 |
| 50 | 1.78 ± 0.16 |
| 500 | 0.37 ± 0.02 |
| 5,000 | 0.30 ± 0.01 |

EXAMPLE 2

Survival and growth of ATH8 cells in the presence of 2',3'-dideoxynucleosides, when exposed to HTLV-III/-LAV: $2 \times 10^5$ ATH8 cells were treated with polybrene, exposed to HTLV-III$_B$ (2,000 virus particles/cell), resuspended in culture tubes, and cultured (solid symbols) in the presence or absence (a) of 50 μM 2',3'-dideoxyadenosine (Calbiochem-Behring Corp., La Jolla, Calif.) (b), 50 μM 2',3'-dideoxyinosine (Calbiochem-Behring Corp.) (c), 1 μM 2',3'-dideoxythymidine (P.L. Biochemicals Inc., Milwaukee, Wis.) (e). Control cells were similarly treated but were not exposed to the virus (open symbols). At various time points, total viable cells were counted as described in Example 1. The results are illustrated in FIG. 1.

EXAMPLE 3

Figure 2:
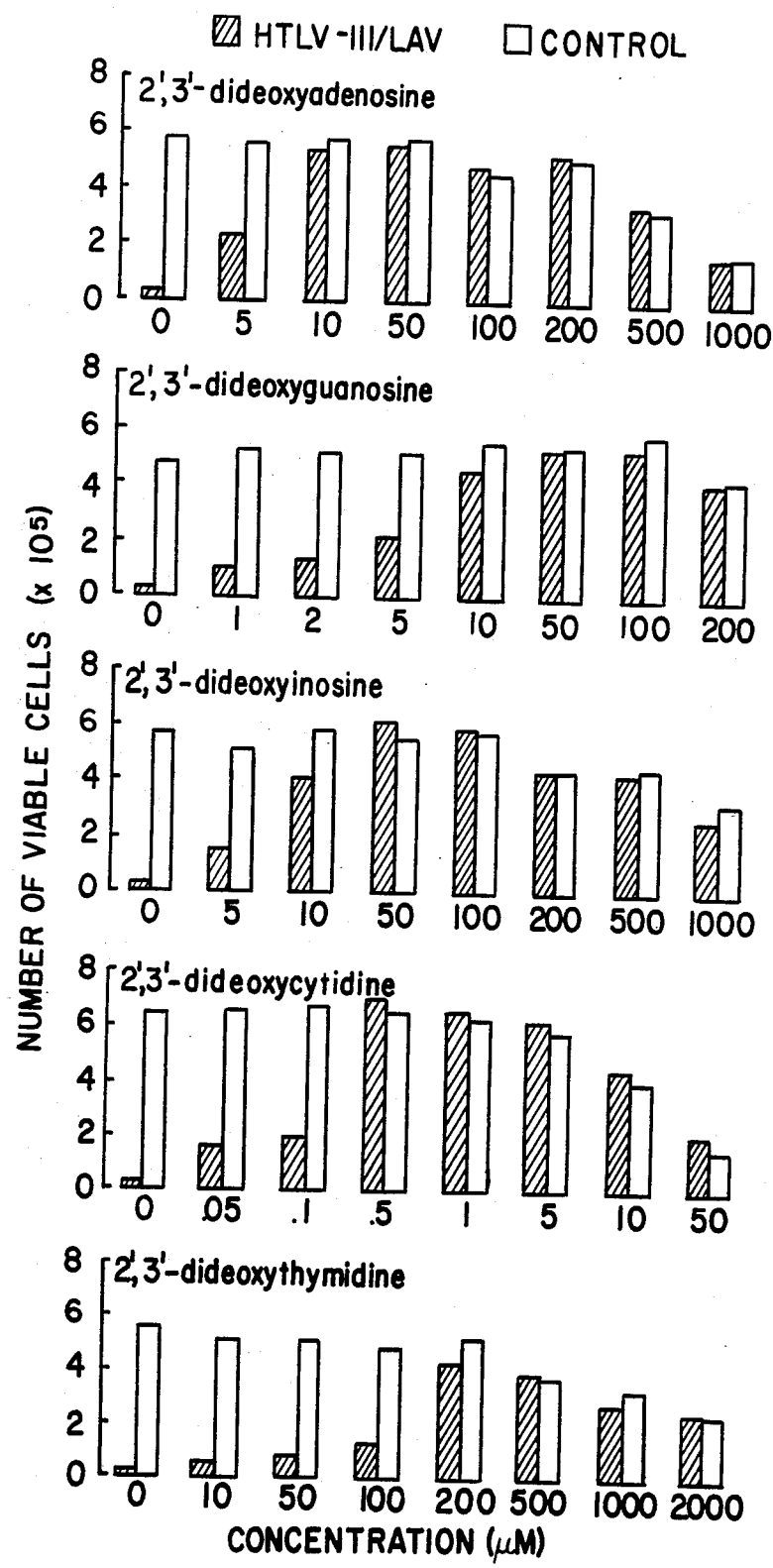
FIG. 2 shows the inhibition of cytopathic effect of HTLV-III/LAV by 2',3'-dideoxynucleosides against ATH8 cells.

Inhibition of cytopathic effect of HTLV-III/LAV by 2',3'-dideoxynucleosides against ATH8 cells: $2 \times 10^5$ ATH8 cells were pre-exposed to polybrene, exposed to HTLV-III$_B$ (2,000 virus particles/cell) in culture tubes (solid columns) in the presence or absence of various concentrations of 2',3'-dideoxyadenosine, -dideoxyinosine, -dideoxyguanosine (P.L. Biochemicals Inc.), -dideoxycytidine, or -dideoxythymidine. Control cells (open columns) were similarly treated but were not exposed to the virus. On day 5, total viable cells were counted as described in Example 1. The results are illustrated in FIG. 2.

The same test experiment was performed for adenosine congeners (see FIG. 3): 2',3'-dideoxyadenosine (a), 2'-deoxyadenosine (Calbiochem-Behring Corp.) (b), 3'-deoxyadenosine (cordycepin; Behringer-Mannheim GmbH, West Germany) (c), and adenosine arabinoside (d) and 2',3',5'-trideoxyadenosine (e). The primed numbers in (a) refer to positions in the sugar moiety. Control cells (open columns) were not exposed to the virus. On day 5, the total viable cells were counted as described in Example 1.

EXAMPLE 4

Figure 4:
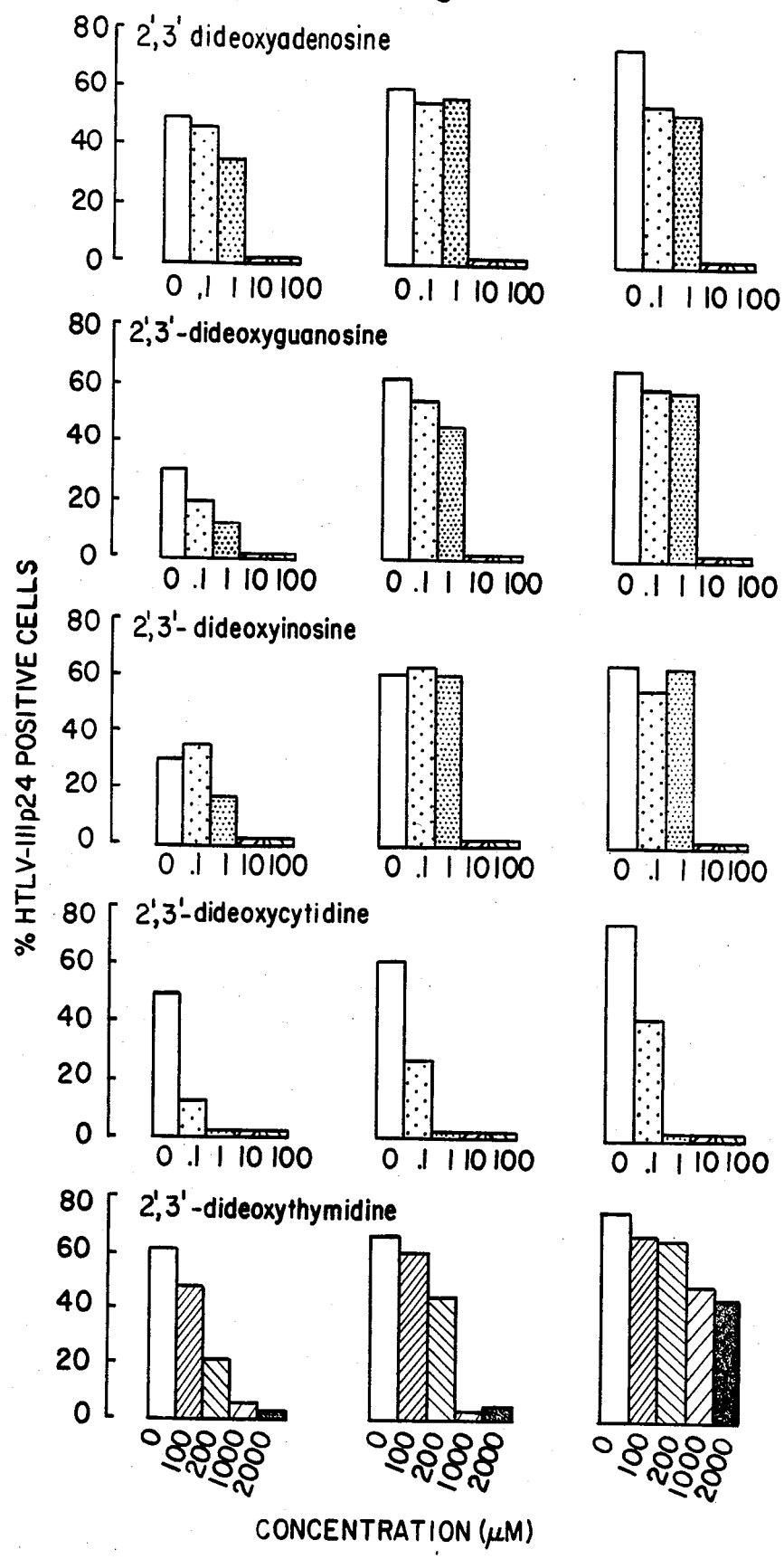
FIG. 4 shows the inhibition of the infectivity and replication of HTLV-III/LAV in H9 cells by 2',3'-dideoxynucleosides.

Inhibition of the infectivity and replication of HTLV-III/LAV in H9 cells by 2',3'-dideoxynucleosides: $10^5$ H9 cells were exposed to various concentrations of 2',3'-dideoxynucleosides for 4 hours, then to 2 ug/ml polybrene for 30 minutes, pelleted, and exposed to HTLV-III$_B$ (3,000 virus particles/cell) for 1.5 hours. Cells were resuspended in fresh complete medium and cultured in tubes at 37° C. in 5% $CO_2$-containing humidified air. The cells were continuously exposed to 2',3'-dideoxynucleosides. On days 8 (left), 9 (middle), and 10 (right) in culture, the percentage of the taret H9 cells expressing p24 gag protein of HTLV-III/LAV was determined by indirect immunofluorescence microscopy by using anti-HTLV-III/LAV p24 murine monoclonal. The results are illustrated in FIG. 4.

EXAMPLE 5

Using the process of this invention, ATH8 was compared to other clones--CEM, MT-2, and MT-4 cells. It was found that ATH8 cells are killed by the cytopathic effect of HTLV-III within 4-5 days after exposure to HTLV-III. On the other hand, it took 9-10 days for CEM cells to be killed by HTLV-III cytopathic effect. Furthermore, CEM cells began to grow on days 12-13 in culture, indicating that this cell line contains heterogenous populations.

MT-2 and MT-4 cells seem to be approximately as sensitive as ATH8 cells against cytopathic effect of HTLV-III. However, MT-2 and MT-4 cells cannot be rescued by anti-HTLV-III agents. Both MT-2 and MT-4 cells were derived from cord blood lymphocytes that were cocultured with leukemic cells from patients with ATL. Therefore, those lines are mixed populations of sensitive and insensitive lymphocytes against HTLV-III. Furthermore, MT-2 is known to produce very high titer of HTLV-I virions in vitro; these virions reinfect MT-2 cells in vitro which increases the instability of the characteristics of the cell line.

ATH8 is a cloned cell line, which has advantages over other cell lines (CEM, MT-2 and MT-4) as follows: (a) easy to handle because it is an HTLV-I non producer; (b) never survives the cytopathic effect of HTLV-III; (c) stable characteristics because it is a homogeneous cloned cell line; and (d) less chance of reinfection by HTLV-I.

We claim:

1. A cloned OKT4+ HTLV-I-transformed lymphocyte cell line having all of the identifying characteristics of ATH8 (CRL-9221).

2. A process for assaying the HTLV-III-inhibiting activity of a test drug or other agent comprising the steps of:

(a) suspending in an appropriate culture medium cells of the ATH8 cloned cell line, a measured amount of HTLV-III virus sufficient to infect and lyse said ATH8 cells, and said test drug or agent;
(b) incubating the suspension of step (a) up for to ten days and
(c) counting the number of viable ATH8 cells remaining after completion of the incubation period, wherein the number of viable ATH8 cells is an indication of the HTLV-III-inhibiting activity of the test drug or agent.

3. The process of claim 2 wherein the test drug or agent is 2',3'-dideoxycytidine, 2',3'-dideoxyadenosine, 2',3'-dideoxyguanosine, or 2',3'-dideoxyinosine.

4. A composition of matter consisting essentially of cells of the cloned cell line of claim 1 and a growth media therefor.

* * * * *

UNITED STATES PATENT AND TRADEMARK OFFICE
CERTIFICATE OF CORRECTION

PATENT NO. : 4,704,357
DATED : November 3, 1987
INVENTOR(S) : Mitsuya et al

It is certified that error appears in the above-identified patent and that said Letters Patent is hereby corrected as shown below:

In claim 2, paragraph B, please change "up for to ten" to --for up to ten--

Signed and Sealed this

Second Day of August, 1988

Attest:

DONALD J. QUIGG

Attesting Officer

Commissioner of Patents and Trademarks